United States Patent
Farge et al.

[11] Patent Number: 4,550,110
[45] Date of Patent: Oct. 29, 1985

[54] 6-(1,8-NAPHTHYRIDIN-2-YL)-DITHINO[1,4][2,3-c]-PYRROLES USEFUL AS TRANQUILLIZERS AND ANTICONVULSANTS

[75] Inventors: Daniel Farge, Thiais; André Léger, Paris; Gerard Ponsinet, Sucy-en-Brie, all of France

[73] Assignee: Rhone-Poulenc Sante, Courbevoie, France

[21] Appl. No.: 487,133

[22] Filed: Apr. 21, 1983

[30] Foreign Application Priority Data

Apr. 22, 1982 [FR] France ................................ 82 06944

[51] Int. Cl.⁴ .................. C07D 401/14; A61K 31/495
[52] U.S. Cl. .................................... 514/254; 544/362; 544/373
[58] Field of Search ................. 544/362, 373; 424/250

[56] References Cited

U.S. PATENT DOCUMENTS 4,220,646  9/1980  Cotrel et al. ........................ 544/373

OTHER PUBLICATIONS

Wolff, M. E., "Burger's Medicinal Chemistry", Part I, 4 ed., (1980), pp. 169-171, John Wiley & Sons, N.Y.

*Primary Examiner*—Donald G. Daus
*Assistant Examiner*—S. A. Gibson
*Attorney, Agent, or Firm*—Stevens, Davis, Miller & Mosher

[57] ABSTRACT

New compounds of the formula

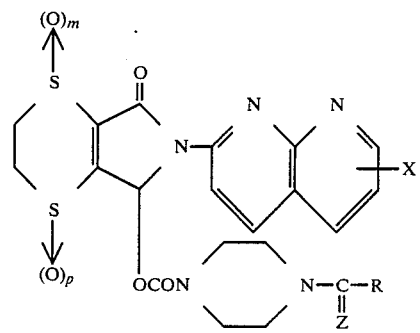

wherein X represents hydrogen, halogen, alkyl (1 to 4 C), alkoxy (1 to 4 C), cyano or nitro, R represents hydrogen, alkyl (1 to 4 C) [unsubstituted or substituted by 1, 2 or 3 halogens, alkenyl (2 to 4 C), alkynyl (2 to 4 C) or alkoxy (1 to 4 C)], phenyl [unsubstituted or substituted by 1, 2 or 3 halogens, alkyl (1 to 4 C), alkoxy (1 to 4 C), nitro or trifluoromethyl] or phenylalkyl (1 to 4 C) or phenylalkynyl (2 to 4 C) in which the phenyl radicals are optionally substituted as indicated above, Z represents an oxygen or sulphur atom, and one of m and p represents the figure 0 and the other the figure 1.

The new compounds are therapeutically useful, more particularly as tranquillizers and anticonvulsants.

6 Claims, No Drawings

6-(1,8-NAPHTHYRIDIN-2-YL)-DITHIINO[1,4][2,3-C]-PYRROLES USEFUL AS TRANQUILLIZERS AND ANTICONVULSANTS

DESCRIPTION

This invention relates to new therapeutically useful dithiino[1,4][2,3-c]pyrrole derivatives, to a process for their preparation and pharmaceutical compositions containing them.

The new dithiino[1,4][2,3-c]pyrrole derivatives of the present invention are those of the general formula:

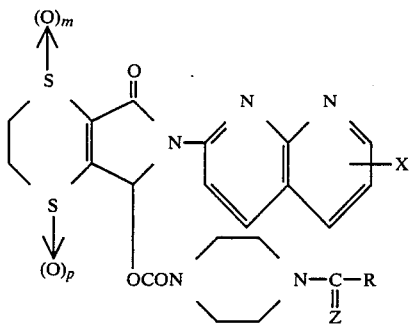

wherein X represents a hydrogen or halogen, preferably chlorine, atom or an alkyl or alkoxy radical containing 1 to 4 carbon atoms, a cyano radical or a nitro radical, R represents a hydrogen atom, an alkyl radical containing 1 to 4 carbon atoms which is unsubstituted or substituted by one, two or three halogen atoms, an alkenyl radical containing 2 to 4 carbon atoms, an alkynyl radical containing 2 to 4 carbon atoms, or an alkoxy radical containing 1 to 4 carbon atoms, or R represents a phenyl radical which is unsubstituted or substituted by one, two or three halogen atoms, an alkyl radical containing 1 to 4 carbon atoms, an alkoxy radical containing 1 to 4 carbon atoms, a nitro radical or a trifluoromethyl radical, or alternatively a phenylalkyl radical in which the alkyl moiety contains 1 to 4 carbon atoms, or a phenylalkynyl radical in which the alkynyl moiety contains 2 to 4 carbon atoms, and in which the phenyl nuclei are optionally substituted as indicated above, Z represents an oxygen or sulphur atom, and one of the symbols m and p represents the figure 0 and the other represents the figure 1.

It is to be understood that the aforementioned alkyl, alkenyl and alkynyl radicals, or alkyl or alkynyl moieties of phenylalkyl and phenylalkynyl radicals, mentioned above in respect of the definitions of symbols X and R may have straight-chains or branched-chains.

It is also to be understood that the present invention relates to the compounds of general formula I in the cis and trans forms, either pure or as mixtures.

According to a feature of the invention, the compounds of general formula I are obtained by oxidising one of the sulphur atoms of a compound of the general formula:

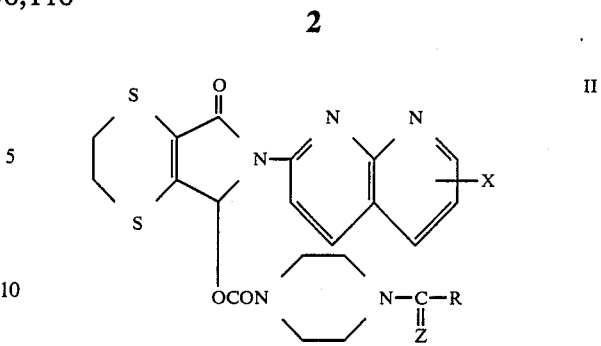

wherein X, R and Z are as hereinbefore defined, to an —SO— radical, and then separating the products obtained.

The oxidation can be carried out using one equivalent of an agent commonly used for converting a sulphide to a sulphoxide, the reaction being carried out in a suitable solvent. By way of example, it is possible to use hydrogen peroxide in acetone or acetic acid, an alkali metal periodate in an alcohol or acetonitrile, or a peroxycarboxylic acid, e.g. peracetic, perbenzoic, m-chloroperbenzoic, p-nitroperbenzoic or perphthalic acid, in an ether (e.g. dioxan, tetrahydrofuran or diethyl ether), a chlorinated solvent (e.g. methylene chloride or dichloroethane), acetic acid or a mixture of these solvents. The reaction is generally carried out at a temperature between −10° and +20° C.

It is particularly advantageous to carry out the reaction in a mixture of acetic acid and methylene chloride, in the presence of m-chloroperbenzoic acid, at a temperature between −10° and 0° C.

The separation of the various oxidation products can be carried out by any customary physical or chemical means known to those skilled in the art. It is particularly advantageous to carry out the separation by chromatography.

The starting materials of general formula II can be prepared as described in U.S. Pat. No. 4220646 or British Pat. No. 1468497.

Of particular value are the compounds of general formula I wherein X represents a halogen atom, Z represents an oxygen atom, R represents an alkyl radical containing 1 to 4 carbon atoms, and m and p are as hereinbefore defined, and more particularly 6-(7-chloro-1,8-naphthyridin-2-yl)-5-(4-propionylpiperazin-1-yl)-carbonyloxy-7-oxo-2,3,6,7-tetrahydro-5H-dithiino[1,4][2,3-c]pyrrole 1-oxide and 6-(7-chloro-1,8-naphthyridin-2-yl)-5-(4-propionylpiperazin-1-yl)carbonyloxy-7-oxo-2,3,6,7-tetrahydro-5H-dithiino[1,4]-[2,3-c]pyrrole 4-oxide.

The dithiino[1,4][2,3-c]pyrrole compounds of general formula II have a tranquilliser, anticonvulsant and hypnogenic action. It has now been found that the new compounds according to the present invention, i.e. the corresponding monosulphoxides, possess a tranquillising and anticonvulsant activity similar to that of the compounds of general formula II but have weaker "hypnogenic" properties which render them more suitable for the treatment of certain maladies, for example, anxiety states and epilepsy.

The tranquillising activity of the compounds according to the present invention can be demonstrated on animals, viz mice, at doses of between 1 to 10 mg/kg, administered orally, in the pentetrazole-induced convulsions tests, in accordance with a technique similar to that of Everett and Richards, *J. Pharmacol.Exp.-Ther.* 81,402(1964).

In mice, by oral administration, in the test for potentiation of a low dose of chlorpromazine, measured in the Righting Reflex test, according to Zbinden and Randall, Advances in Pharmacology 5, 213–291 (1967) a test making it possible to predict the "hypnogenic" effects of a product, the products were only shown to be active at doses of more than 30 mg/kg.

Furthermore, the products according to the present invention have a low toxicity. In mice, the acute toxicity, expressed by its $LD_{50}$, is generally between 300 and 900 mg/kg or even more than 900 mg/kg.

The following non-limitative Example illustrates the preparation of compounds of the present invention.

EXAMPLE 1

A solution of 80% pure 3-chloroperbenzoic acid (2.32 g) in methylene chloride (65 cc) is added to a solution of 6-(7-chloro-1,8-naphthyridin-2-yl)7-oxo-5-(4-propionylpiperazin-1-yl)carbonyloxy-2,3,6,7-tetrahydro5H-dithiino[1,4][2,3-c]pyrrole (5 g) in methylene chloride (100 cc), cooled to −10° C. The addition is carried out dropwise in the course of 30 minutes so as to keep the temperature at between −10° and −5° C. Stirring is continued for a further one hour at this temperature and the solution is then poured into diethyl ether (400 cc) cooled to 0° C. The precipitate which forms is filtered off, washed with diethyl ether (60 cc) and dried in air.

The product obtained is chromatographed on silica gel (0.04–0.06 mm; 100 g) contained in a column of diameter 4 cm. Elution is carried out with a mixture of chloroform (2910 cc) and methanol (90 cc), 70 cc fractions being collected.

Fractions 5 to 19 are combined and concentrated to dryness under reduced pressure (20 mm Hg; 2.7 kPa) at 40° C. The residue is triturated in diisopropyl ether (30 cc). The solid obtained is filtered off, washed with diisopropyl ether (10 cc) and dried under reduced pressure (0.2 mm Hg; 0.027 kPa) at 40° C. This gives 6-(7chloro1,8-naphthyridin-2-yl)-5-(4-propionylpiperazin-1-yl)carbonyloxy-7-oxo-2,3,6,7-tetrahydro-5H-dithiino[1,4]-[2,3-c]pyrrole 1-oxide (4.3 g), possibly as a mixture of the cis and trans forms, melting with decomposition at 206° C.

Fractions 27 to 39 are combined and concentrated to dryness under reduced pressure (20 mm Hg; 2.7 kPa) at 40° C. The residue is triturated in diisopropyl ether (30 cc). The solid obtained is filtered off, washed with diisopropyl ether (10 cc) and dried under reduced pressure (0.2 mm Hg; 0.027 kPa) at 40° C. This gives 6-(7-chloro1,8-naphthyridin-2-yl)-5-(4-propionylpiperazin-1-yl)carbonyloxy-7-oxo-2,3,6,7-tetrahydro-5H-dithiino[1,4]-[2,3-c]pyrrole 4-oxide (0.5 g) corresponding to the cis or trans form and melting with decomposition at 220° C.

The present invention includes within its scope pharmaceutical compositions comprising at least one of the compounds of general formula I, in association with any other pharmaceutically compatible product, which can be inert or physiologically active. The compositions can be administered orally, parenterally or rectally.

Tablets, pills, powders, in particular in gelatin capsules or in cachets, or granules can be used as solid compositions for oral administration. In these compositions, the active product according to the invention is mixed with one or more inert diluents such as starch, cellulose, sucrose, lactose or silica. These compositions can also comprise substances other than diluents, e.g. one or more lubricants such as magnesium stearate or talc, a dyestuff, a coating, as in coated tablets, or a varnish.

Liquid compositions for oral administration include pharmaceutically acceptable solutions, suspensions, emulsions, syrups and elixirs containing inert diluents commonly used in the art, such as water, ethanol, glycerol, vegetable oils or paraffin oil. These compositions can also comprise substances other than diluents, e.g. wetting, sweetening, thickening, flavouring or stabilising products.

Pharmaceutical compositions for parenteral administration include sterile aqueous or non-aqueous solutions, suspensions or emulsions. Examples of suitable non-aqueous solvents or vehicles are propylene glycol, a polyethylene glycol, vegetable oils, in particular olive oil, and injectable organic esters such as ethyl oleate. These compositions can also contain adjuvants, in particular wetting agents, agents for imparting isotonicity, emulsifiers, dispersants and stabilisers. Sterilisation can be carried out in several ways, e.g. by aseptic filtration, by incorporating sterilising agents into the composition, by irradiation or by heating. The compositions can also be prepared in the form of sterile solid compositions which can be dissolved in an injectable sterile medium at the time of use.

The compositions for rectal administration are suppositories or rectal capsules, which contain, in addition to the active product, excipients such as cacao butter, semi-synthetic glycerides or polyethylene glycols.

In human therapy, the compounds of the present invention are particularly useful in the treatment of certain diseases manifesting themselves as anxiety states or epileptiform states. The doses depend on the desired effect and the duration of the treatment; adult doses are generally between 1 and 100 mg per day, administered orally in one or more dosage units.

In general the physician will determine the dosage which he considers to be most appropriate taking into account the age, the weight and all the other factors intrinsic to the patient being treated.

The following Example illustrates pharmaceutical compositions according to the invention.

EXAMPLE 2

Tablets containing 10 mg doses of active product and having the following composition are prepared by the usual technique:

| | |
|---|---|
| 6-(7-chloro-1,8-naphthyridin-2-yl)-5-(4-propionylpiperazin-1-yl)carbonyloxy-7-oxo-2,3,6,7-tetrahydro-5H-dithiino[1,4]-[2,3-c]pyrrole 1-oxide | 10 mg |
| starch | 60 mg |
| lactose | 50 mg |
| magnesium stearate | 2 mg |

We claim:

1. A pure [1,4][2,3-c]pyrrole of the formula:

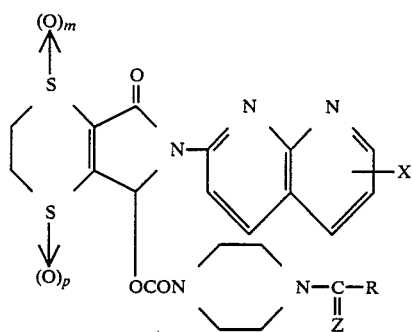

wherein X represents a hydrogen or halogen atom, or an alkyl or alkoxy radical containing 1 to 4 carbon atoms, a cyano radical or a nitro radical, R represents a hydgrogen atom, an alkyl radical containing 1 to 4 carbon atoms which is unsubstituted or substituted by one, two or three halogen atoms, an alkenyl radical containing 2 to 4 carbon atoms, an alkynyl radical containing 2 to 4 carbon atoms or an alkoxy radical containing 1 to 4 carbon atoms, or R represents a phenyl radical which is unsubstituted or substituted by one, two or three halogen atoms, an alkyl radical containing 1 to 4 carbon atoms, an alkoxy radical containing 1 to 4 carbon atoms, a nitro radical or a trifluoromethyl radical, or R represents a phenylalkyl radical in which the alkyl moiety contains 1 to 4 carbon atoms, or a phenylalkynyl radical in which the alkynyl moiety contains 2 to 4 carbon atoms, and in which the phenyl nuclei are optionally substituted as indicated above, Z represents an oxygen or sulphur atom, and one of the symbols m and p represents the figure O and the other represents the figure 1.

2. A pure [1,4][2,3-c]pyrrole according to claim 1 wherein X represents a halogen atom, Z represents an oxygen atom, R represents an alkyl radical containing 1 to 4 carbon atoms, and m and p are as defined in claim 1.

3. A pure compound according to claim 1 which is 6-(7-chloro-1,8-naphthyridin-2-yl)-5-(4-propionyl-piperazin1-yl)-carbonyloxy-7-oxo-2,3,6,7-tetrahydro-5H-dithiino[1,4]-[2,3-c]pyrrole 1-oxide.

4. A pure compound according to claim 1 which is 6-(7-chloro-1,8-naphthyridin-2-yl)-5-(4-propionyl-piperazin1-yl)-carbonyloxy-7-oxo-2,3,6,7-tetrahydro-5H-dithiino[1,4]-[2,3-c]pyrrole 4-oxide.

5. A pharmaceutical composition useful as a tranquillizer or anticonvulsant which comprises a dithiino[1,4][2,3-c]pyrrole as claimed in claim 1, 2, 3, or 4 in association with a pharmaceutical carrier.

6. A method for the treatment of a patient suffering from an anxiety state or an epileptiform state which comprises administering to the patient a tranquilliser or anticonvulsant of the formula depicted in claim 1, wherein X, R, Z, m and p are as defined in claim 1, sufficient to ameliorate the condition of the patient.

* * * * *